United States Patent

Rickauer

[11] Patent Number: 6,022,375
[45] Date of Patent: Feb. 8, 2000

[54] BREAST PROSTHESIS

[75] Inventor: Peter Rickauer, Bernau, Germany

[73] Assignee: DEKUMED Gesellschaft fur Kunststoff- und Medizintechnik mbH, Bernau, Germany

[21] Appl. No.: 08/644,525

[22] Filed: May 10, 1996

Related U.S. Application Data

[63] Continuation of application No. 08/144,773, Oct. 29, 1993, abandoned.

[30] Foreign Application Priority Data

Oct. 30, 1992 [DE] Germany .................. 92 14 775 U

[51] Int. Cl.$^7$ ....................................... A61F 2/52
[52] U.S. Cl. ................................................. 623/7
[58] Field of Search .................. 623/7, 8, 11, 17

[56] References Cited

U.S. PATENT DOCUMENTS

| | | |
|---|---|---|
| 2,108,205 | 2/1938 | Martin .......................... 623/8 |
| 3,576,037 | 4/1971 | Klein . |
| 4,597,763 | 7/1986 | Schweikhart ................. 623/8 |
| 5,282,856 | 2/1994 | Ledergerber ................. 623/8 |

FOREIGN PATENT DOCUMENTS

| | | |
|---|---|---|
| 0320590 | 6/1989 | European Pat. Off. ............ 623/7 |
| 2605148 | 8/1977 | Germany . |
| 3938328 | 11/1989 | Germany . |
| 9107681 | 1/1992 | Germany . |
| 9206370 | 8/1992 | Germany . |
| 9213880 | 2/1993 | Germany . |
| 0484367 | 5/1938 | United Kingdom ............ 623/8 |
| 933052 | 3/1962 | United Kingdom . |
| 8601997 | 4/1986 | WIPO . |

*Primary Examiner*—Debra S. Brittingham
*Attorney, Agent, or Firm*—Robert W. Becker & Associates

[57] ABSTRACT

A breast prosthesis in the form of an elongated body tapering off towards both ends is substantially made of a hardened plastic resin with gel properties and has a convex upper surface and a substantially planar to slightly convex lower surface, whereby the upper and the lower surfaces in a plan view of the body are delimited by two circular arcs intercepting one another at two points of interception.

4 Claims, 1 Drawing Sheet

BREAST PROSTHESIS

This application is a continuation of application Ser. No. 08/144,773 filed Oct. 29, 1993, now abandoned.

BACKGROUND OF THE INVENTION

The present invention relates to a breast prosthesis. Such breast prosthesis are, for example, used as a support for a breast that deviates from the ideal shape or for enlarging small-sized breasts or as a prosthesis after breast surgery. These breast prosthesis commonly are comprised of foamed plastic material and are sewn into pockets of brassieres. From German Gebrauchsmuster 91 07 681.1 a breast prosthesis is known which is comprised of a soft two-component silicone rubber material with a soft gel-type consistency that is enclosed in plastic foil fused together. These prostheses may have substantially the same thickness over their length or they may have varying mass distributions. More defined descriptions of the special embodiment of these prostheses however are not provided.

From German Gebrauchsmuster 92 06 370.5 a breast prosthesis with a body comprised of a two-component silicone rubber that is cross-linked by an addition reaction and that is enclosed in a polyurethane film is known. This prior art breast prosthesis has a convex front side and a substantially concave backside which rests at the contour of the female breast. The breast prosthesis is provided with an adhesive connected fixedly to the breast prosthesis and detachably connectable to the female breast.

Such a breast prosthesis is designed, for example, to correct the appearance of partly amputated breasts. Such breast prosthesis, however, has the disadvantage that an ideal shape correction of the partly amputated breast is not possible.

Breast surgery in early stages of breast cancer is performed commonly such that not the entire breast is removed, but that only the portion of the breast attacked by the cancer growth is amputated. At these locations flattened portions or depressions are produced that must be compensated so that the partly amputated breast again assumes the shape of the non-amputated breast.

It is therefore an object of the present invention to provide a breast prosthesis with which the aforementioned disadvantages can be overcome.

BRIEF DESCRIPTION OF THE DRAWINGS

This object, and other objects and advantages of the present invention, will appear more clearly from the following specification in conjunction with the accompanying drawings, in which.

SUMMARY OF THE INVENTION

The breast prosthesis of the present invention is in the form of an elongated body tapering off toward both ends, comprised of a hardened plastic resin with gel properties and having a convex upper surface and a substantially planar to slightly convex lower surface, the upper and the lower surfaces in a top view of the body delimited by two circular arcs intercepting one another at two points of interception.

Preferably, the radius of curvature of the two intercepting circular arcs are substantially identical.

In a preferred embodiment of the present invention, the radius of curvature of one of the two intercepting circular arcs is substantially identical to a radius of curvature of the upper surface in a longitudinal direction of the elongated body and is substantially twice as great as a radius of curvature of the upper surface in cross-section transverse to the longitudinal direction at a center portion of the body.

Advantageously, the circular arcs in the vicinity of the points of interception are shaped to form a circular transition into one another.

According to the present invention the breast prosthesis is in the form of an elongated body which tapers off toward its ends and is comprised of a gel-type hardened plastic resin material. This breast prosthesis inventively is provided with a convex upper surface and a substantially planar to slightly convex lower surface, whereby these two surfaces, in a plan view, are delimited by two intercepting circular arcs.

This breast prosthesis rests with its planar to slightly convex lower surface on the part of the breast that has undergone amputation and generates with its convex upper surface a curvature which corresponds to the curvature of the non-amputated breast.

The size of the breast prosthesis may be adapted to the operatively removed portion of the cancer growth.

Description of Preferred Embodiments

The present invention will now be described in detail with the aid of several specific embodiments utilizing FIGS. 1 to 3A.

Figure 1:
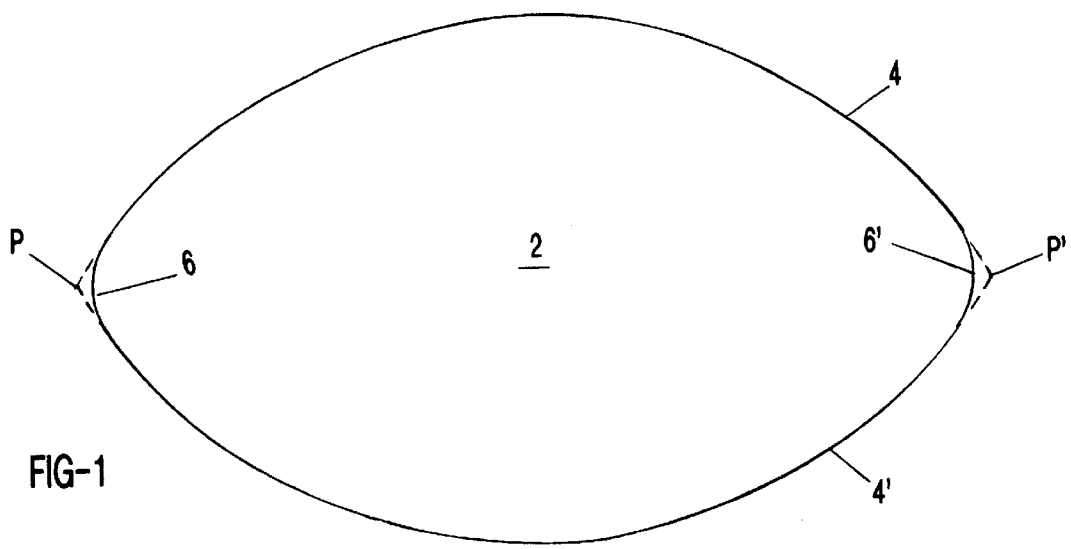
FIG. 1 shows the breast prosthesis in a plan view.

FIG. 1 shows in a top view the convex upper surface 2 which is delimited by two intercepting circular arcs 4, 4'. These two intercepting circular arcs have a theoretical point of interception at points P, P' as indicated by the dashed lines in the drawing. In practice, however, the two circular arcs in the vicinity of these points have a circular transition 6, 6' into one another, as shown in FIG. 1.

Figure 2:
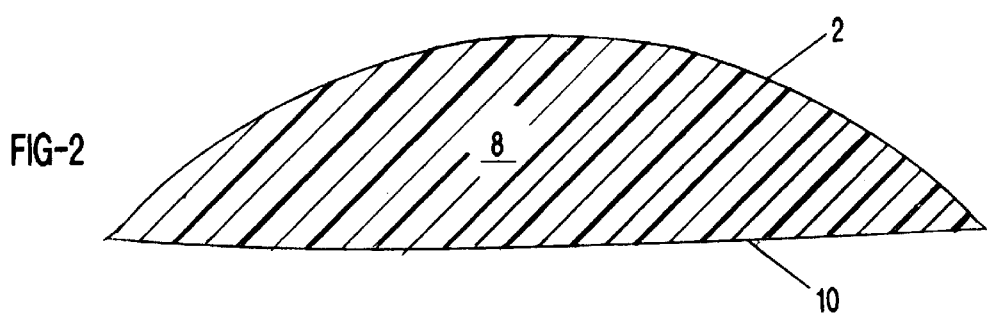
FIG. 2 shows a longitudinal section of the breast prosthesis of FIG. 1.

In the longitudinal section of FIG. 2 the body 8 is shown as a gel-type hardened plastic resin. The body 8 is preferably comprised of a silicone resin material that is hardened, respectively, cross-linked (cured) by addition or condensation reactions. This silicone resin material may be used without an enclosure (envelope) made of a film or foil. However, this has the disadvantage that the body 8 could be tacky since the silicone resin material often is not completely cross-linked. Advantageously, the silicon resin material is thus enclosed by a foil, as is described in detail in connection with FIG. 3A in the following.

The silicone resin body 8 is delimited by the convex upper surface 2 and the substantially planar to slightly convex lower surface 10. This is also shown in the cross-sectional representation of the breast prosthesis of FIG. 3.

Figure 3:
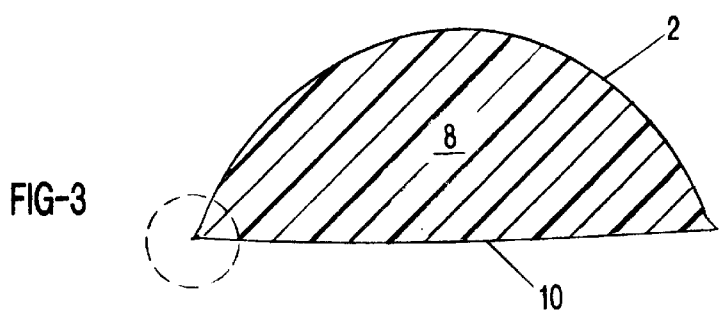
FIG. 3 shows a cross-sectional view of the breast prosthesis of FIG. 1.
Figure 3A:
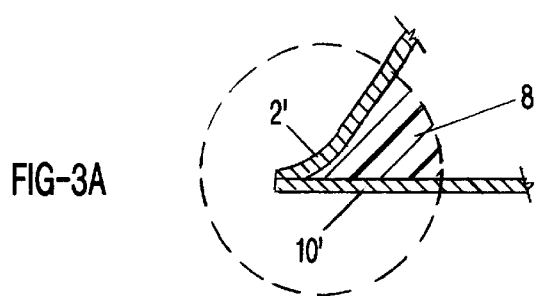
FIG. 3A shows a detailed cross-section of the edge portion of FIG. 3.

In the represented embodiment, the radii of curvature of the circular arcs 4, 4' are substantially identical. These radii of curvature are also substantially identical to the radius of curvature of the upper surface 2 of FIG. 2 and substantially twice as great as the radius of curvature of the upper surface 2 as shown in FIG. 3. The detailed cross-sectional representation of FIG. 3A shows how the body 8 made of silicone resin material is enclosed between two foils 2' and 10', for example, made of polyurethane foil, which in the shown embodiment represent the convex upper surface, respectively, the substantially planar lower surface.

The manufacture of the foil-enclosed breast prosthesis according to the aforedescribed embodiments can be carried out according to German Patent 3 938 328, the disclosure of which is hereby enclosed by reference. In this method, in a first step the foil (reference numeral 2' of FIG. 3A), which represents the foil facing away from the human body, is stretched over a matrix having a contour that corresponds to the desired shape of the convex upper surface 2. The plastic foil is then adapted to the contour of the matrix by deep-drawing. The matrix is subsequently filled to its rim with the plastic resin material 8. In the next step, the plastic resin material is covered by a second foil (reference numeral 10' of FIG. 3A) and is fused along its entire edge to the first foil. The plastic resin body 8 is subsequently hardened, respectively, cross-linked (cured).

The present invention is, of course, in no way restricted to the specific disclosure of the specification and drawings, but also encompasses any modifications within the scope of the appended claims.

What I claim is:

1. An external breast prosthesis to be placed into a brassiere for replacing a surgically removed portion of a breast; said external breast prosthesis comprising:

an elongated body with a first and a second end, said elongated body tapering off toward said first and second ends;

said body having a convex upper surface and a planar to slightly convex lower surface;

said upper and said lower surfaces in a top view of said body delimited by two circular arcs intercepting one another at two points of interception;

said body comprised of a silicone resin material with gel properties that is cross-linked by addition or condensation reactions and a first foil and a second foil;

said first foil covering said lower surface and having an edge projecting past said lower surface;

said second foil covering said convex upper surface and projecting past said convex upper surface;

wherein said edge of said first foil and said edge of said second foil are fused together to enclose said silicone resin material with gel properties.

2. A breast prosthesis according to claim 1, wherein a radius of curvature of said two intercepting circular arcs is substantially identical.

3. A breast prosthesis according to claim 1, wherein a radius of curvature of one of said two intercepting circular arcs is substantially identical to a radius of curvature of said upper surface in a longitudinal direction of said elongated body and is substantially twice as great as a radius of curvature of said upper surface in cross-section transverse to said longitudinal direction at a center portion of said body.

4. A breast prosthesis according to claim 1, wherein said circular arcs in the vicinity of said points of interception are shaped to form a circular transition into one another.

* * * * *